United States Patent [19]

Baumbach et al.

[11] Patent Number: 5,831,003

[45] Date of Patent: Nov. 3, 1998

[54] PEPTIDES WHICH BIND TO PROTHROMBIN AND THROMBIN

[75] Inventors: George A. Baumbach, Knightdale; Christopher A. Dadd, Cary; Joseph A. Buettner; David J. Hammond, both of Raleigh, all of N.C.

[73] Assignee: Bayer Corporation, Berkeley, Calif.

[21] Appl. No.: 672,805

[22] Filed: Jun. 28, 1996

[51] Int. Cl.⁶ ........................................................ C07K 7/00
[52] U.S. Cl. ........................................... 530/329; 530/384
[58] Field of Search ...................................... 530/329, 384

[56] References Cited

U.S. PATENT DOCUMENTS 5,367,060  11/1994  Vanalen et al. ........................ 530/399

*Primary Examiner*—Cecilia J. Tsang
*Assistant Examiner*—C. Delacroix-Muirheid
*Attorney, Agent, or Firm*—Michael J. Beck; James A. Giblin

[57] ABSTRACT

Peptide ligands which bind to thrombin and prothrombin are disclosed. The sequences of these peptides are Gln-Leu-Trp-Gly-Ser-His, Arg-Gln-Leu-Trp-Gly-Ser-His, His-Gln-Leu-Trp-Gly-Ser-His, and Tyr-Phe-Pro-Gly-Pro-Tyr-Leu. The preferred peptides have the sequence Gln-Leu-Trp-Gly-Ser-His or Tyr-Phe-Pro-Gly-Pro-Tyr-Leu. A method of using these peptides in an affinity chromatography process to purify thrombin is described.

2 Claims, 7 Drawing Sheets

- 200,000 dal
- 116,300 dal
- 97,400 dal
- 66,300 dal
- 55,400 dal
- 36,500 dal
- 21,500 dal

SEQUENCE LISTING ( 1 ) GENERAL INFORMATION:

( i i i ) NUMBER OF SEQUENCES: 21

( 2 ) INFORMATION FOR SEQ ID NO:1:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:1:

Gln Leu Trp Gly Ser His
1               5

( 2 ) INFORMATION FOR SEQ ID NO:2:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:2:

Pro Phe Pro Tyr Gly Trp
1               5

( 2 ) INFORMATION FOR SEQ ID NO:3:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:3:

Val Phe Pro Tyr Gly Trp
1               5

( 2 ) INFORMATION FOR SEQ ID NO:4:

( i ) SEQUENCE CHARACTERISTICS:

(A) LENGTH: 6
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:4:

Pro Phe Pro Tyr Ala Trp
1               5

(2) INFORMATION FOR SEQ ID NO:5:

(i) SEQUENCE CHARACTERISTICS:
        (A) LENGTH: 6
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:5:

Val Phe Pro Tyr Ala Trp
1               5

(2) INFORMATION FOR SEQ ID NO:6:

(i) SEQUENCE CHARACTERISTICS:
        (A) LENGTH: 6
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:6:

Pro Phe Pro Tyr Val Trp
1               5

(2) INFORMATION FOR SEQ ID NO:7:

(i) SEQUENCE CHARACTERISTICS:
        (A) LENGTH: 6
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:7:

Val Phe Pro Tyr Val Trp
1               5

(2) INFORMATION FOR SEQ ID NO:8:

(i) SEQUENCE CHARACTERISTICS:
        (A) LENGTH: 6
        (B) TYPE: amino acid
        (C) STRANDEDNESS: single strand
        (D) TOPOLOGY: linear (ii) MOLECULE TYPE:
        (A) DESCRIPTION: peptide (xi) SEQUENCE DESCRIPTION: SEQ ID NO:8:

Val Thr Pro Phe Ala Val
1               5

( 2 ) INFORMATION FOR SEQ ID NO:9:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:9:

Leu Thr Pro Phe Ala Val
 1               5

( 2 ) INFORMATION FOR SEQ ID NO:10:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:10:

Tyr Thr Pro Phe Ala Val
 1               5

( 2 ) INFORMATION FOR SEQ ID NO:11:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:11:

Leu Phe Ala Pro Tyr Leu
 1               5

( 2 ) INFORMATION FOR SEQ ID NO:12:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:12:

Pro Phe Ala Pro Tyr Leu
 1               5

( 2 ) INFORMATION FOR SEQ ID NO:13:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide ( x i ) SEQUENCE DESCRIPTION: SEQ ID NO:13:

Ser Val Arg Pro Phe Leu
1               5

( 2 ) INFORMATION FOR SEQ ID NO:14:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:14:

Phe Glu Pro Ala Asn Pro
1               5

( 2 ) INFORMATION FOR SEQ ID NO:15:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:15:

Gly Phe Arg Lys Gly Pro
1               5

( 2 ) INFORMATION FOR SEQ ID NO:16:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:16:

Gly Phe Arg Gln Gly Pro
1               5

( 2 ) INFORMATION FOR SEQ ID NO:17:

( i ) SEQUENCE CHARACTERISTICS:
        ( A ) LENGTH: 6
        ( B ) TYPE: amino acid
        ( C ) STRANDEDNESS: single strand
        ( D ) TOPOLOGY: linear     ( i i ) MOLECULE TYPE:
        ( A ) DESCRIPTION: peptide     ( x i ) SEQUENCE DESCRIPTION: SEQ ID NO:17:

Glu Arg Pro Tyr His Gly
1               5

( 2 ) INFORMATION FOR SEQ ID NO:18:

( i ) SEQUENCE CHARACTERISTICS:
        ( A ) LENGTH: 6
        ( B ) TYPE: amino acid

```
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:18:

Glu  Arg  Pro  Tyr  Lys  Gly
 1                    5

( 2 ) INFORMATION FOR SEQ ID NO:19:

( i ) SEQUENCE CHARACTERISTICS:
        ( A ) LENGTH: 7
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:19:

Tyr  Phe  Pro  Gly  Pro  Tyr  Leu
 1                    5

( 2 ) INFORMATION FOR SEQ ID NO:20:

( i ) SEQUENCE CHARACTERISTICS:
        ( A ) LENGTH: 7
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:20:

Arg  Gln  Leu  Trp  Gly  Ser  His
 1                    5

( 2 ) INFORMATION FOR SEQ ID NO:21:

( i ) SEQUENCE CHARACTERISTICS:
        ( A ) LENGTH: 7
        ( B ) TYPE: amino acid
        ( C ) STRANDEDNESS: single strand
        ( D ) TOPOLOGY: linear ( i i ) MOLECULE TYPE:
        ( A ) DESCRIPTION: peptide ( x i ) SEQUENCE DESCRIPTION: SEQ ID NO:21:

His  Gln  Leu  Trp  Gly  Ser  His
 1                    5
```

PEPTIDES WHICH BIND TO PROTHROMBIN AND THROMBIN

BACKGROUND OF THE INVENTION

Field

This invention is concerned generally with identifying protein-ligand interactions, and specifically with peptide ligands which bind prothrombin and its activated form, thrombin, and which may be used in a method for the affinity purification of these proteins.

Background

α-Thrombin is the active form of the plasma serine protease zymogen, prothrombin, which has high specificity for Arg-Gly bonds in proteins. α-Thrombin has many physiological substrates, including its endothelial cell receptor, the plasma clotting regulatory protein C, coagulation factors V, VIII and XIII, and the major protein of blood clots, fibrinogen. Cleavage of fibrinogen to fibrin by α-thrombin results in polymerization of fibrin into a blood clot. Thrombin has been used commercially in hemostatic preparations, typically called fibrin glues or sealants.

Purification of thrombin from human plasma was described by Fenton et al. (1977) as derived from the work of Fenton et al. (1971) and Miller and Copeland (1965) using Cohn fraction III as the starting material. The process, which included alkali salt precipitations and cation exchange chromatography, yielded high purity α-thrombin.

Thrombin is also prepared from prothrombin concentrate, also called prothrombin complex concentrate (PTC), which is typically prepared by adsorption and elution of whole plasma from anion exchange resins (summarized in Coan et al., 1981). This fraction is enriched in the zymogen forms of several vitamin-K dependent proteases, including prothrombin (factor II), factors VII, IX and X, protein C, and protein S. Subsequent processing typically involves cation exchange chromatography (Walz and Seegers, 1974; Downing et al. 1975).

Affinity methods have been introduced for high purity enrichment of plasma α-thrombin from prothrombin concentrates or downstream intermediates prepared by cation exchange chromatography. Thrombin has structural features that have been exploited for affinity interactions, namely the catalytic site, the anion-binding site (also known as the fibrinogen-binding exosite I), and the heparin-binding site (exosite II). Useful ligands include synthetic inhibitors, for example chlorobenzylamine (Thompson, 1976; Thompson and Davie, 1971) and p-aminobenzamidine (Lorne et al., 1989; Khamlichi et al., 1990), and substrate analogues, such as L-arginyl methyl ester (Yu et al., 1986), which bind at the catalytic site. Heparin and cation chromatography resins bind at the heparin-binding site (exosite II) (Miller-Anderson et al., 1980; Ngai and Chang, 1991).

Peptide Ligand Chromatography

Although there are many peptide sequences derived from sites on proteins known to interact with and/or be cleaved by thrombin, the inventors know of no references exploiting such peptides for affinity purification of prothrombin or thrombin. Peters et al. (1993) demonstrated the usefulness of modified peptide ligands by using a peptidyl methyl ketone, a recognized class of serine protease inhibitors, for purification of the serine protease thermitase.

Hirudin, a leach anticoagulant protein, has a binding sequence (approximately residues 55–65) which interacts at thrombin's anion binding site (Krstenansky et al., 1987).

Peptide QLWGSH (SEQ ID NO 1), discovered in the present invention for binding to thrombin and factor Xa, has no apparent sequence homology to proteins relevant to thrombin's known functions. For example, homology alignment to proteins in databases revealed no identical matches to QLWGSH but identity of 5 of 6 contiguous residues with superoxide dismutase from *Halobacterium halobium*, uracil-DNA glycosylase (EC 3.2.2.-) from *Escherichia coli*, and 4-alpha-glucanotransferase (EC 2.4.1.25) from *Solanum tuberosum* (potato).

The variant of QLWGSH containing an added amino-terminal histidine (HQLWGSH, SEQ ID NO:21) has no apparent sequence homology to proteins involved with thrombin's known functions. Database searches did not lead to an identical match to HQLWGSH, however the multidrug resistance P-glycoprotein from *Leishmania donovani* was found to have five of seven identical contiguous residues. The search also revealed the aforementioned sequences for QLWGSH. The database search for sequences identical to the QLWGSH variant RQLWGSH (SEQ ID NO:20) revealed no matches. Two sequences with 5 of 7 contiguous identical amino acids were found: early E2A DNA binding protein from human adenovirus and small T antigen from mouse polyomavirus.

Sequence homology searches for the peptide YFPGPYL (SEQ ID NO: 19) revealed no sequence similarities to proteins involved with thrombin's known functions. Three proteins bearing 5 of 7 noncontiguous identical residues were found by the database searches: paraoxonase from *Mus musculus*, starch synthase (EC 2.4.1.11) from *Sorghum bicolor*, and gene p74 protein from *Choristoneura fumiferona*.

SUMMARY OF INVENTION

We have now discovered a group of peptides characterized by their ability to bind to prothrombin and thrombin. This group includes the following peptide affinity ligands: QLWGSH, RQLWGSH, HQLWGSH, and YFPGPYL. (SEQ ID Nos:1, 20, 21, 19, respectively) The preferred ligands are QLWGSH (SEQ ID NO:1) and YFPGPYL (SEQ ID NO:19). We also describe a method of purifying prothrombin and thrombin which comprises passing a protein containing solution over a substrate which has bound upon it a peptide affinity ligand of the defined sequence and then eluting the prothrombin or thrombin.

BRIEF DESCRIPTION OF FIGURES

Lanes 1 and 9, molecular weight standards; lane 2, prothrombin standard; lanes 3 and 8, α-thrombin standards; lane 4, activated PTC eluate; lane 5, unbound fraction; lane 6, 1 M NaCl wash fraction; lane 7, 2% acetic acid eluate.

SPECIFIC EMBODIMENTS

Materials

Monoclonal mouse antibody to thrombin was purchased from American Diagnostica (Greenwich, Conn.). The second antibody conjugate, goat anti-mouse IgG-alkaline phosphatase, and the dye substrates NBT/BCIP and Fast Red TR were from Pierce Chemical Co. (Rockford, Ill.). Human thrombin was purchased from Enzyme Research Labs (South Bend, Ind.). Fmoc amino acids were from Novobiochem (La Jolla, Calif.). All other chemicals were reagent grade or better.

General Methods

Screening of a combinatorial peptide library using the PELICAN strategy (Buettner et al., 1996) was performed in 2.1 mm x 15 cm colums on a microbore HPLC (Microme Bioresources, Auburn, Calif.). Peptides and a 6-mer combinatorial library were synthesized on Toyopearl AF Chelate 650 M (TosoHaas, Montgomeryville, Pa.) modified with 4,7,10-trioxa-1,13-tridecanediamine (Totda; Aldrich, St. Louis, Mont.), using standard Fmoc chemistry as described by Buettner et al. (1996). Peptides were synthesized robotically by using a Gilson AMS 422. Peptide densities achieved with the above strategy were typically in the range of 0.2–0.5 mmole/g resin.

For screening peptides in an affinity chromatographic format, a lower peptide density would be desirable to reduce the risk of peptide-peptide interactions and steric hindrance of thrombin binding to a single peptide. These could result in a decrease in capacity and specificity. Such desirable densities, as practiced in the usual art of affinity chromatography, would be in the range of 0.05 to 0.2 mmole/g resin (10 to 40 mg/ml resin). In order to control the density of peptide synthesized onto the Totda linker, mixtures containing varied ratios of Fmoc-L-alanine to t-Boc-L-alanine were coupled to Totda-Toyopearl. The following mixtures were made: 100% Fmoc-L-alanine; 20% FmocL-alanine/80% t-Boc-L-alanine; 10% Fmoc-L-alanine/90% t-Boc-L-alanine; 4% Fmoc-Lalanine/96% t-Boc-L-alanine; and 1% Fmoc-L-alanine/99 % t-Boc-L-alanine. The total amino acid concentration (plus) was held constant at approximately 2.5 mmole/g resin (five-fold over Totda). After coupling the mixture using standard Fmoc conditions as practiced in the art, the Fmoc protecting group was released by alkali whereas the alkaline resistant t-Boc was not. The residual t-Boc-derivatized L-alanine lacked a primary amine and was not available for further peptide synthesis. Peptides were then synthesized onto the resin using Fmoc-derivitized amino acids, followed by deprotection under acid conditions (which also released the residual t-Boc). The density of peptide on batches of resin was determined by total amino acid analysis of dessicated, weighed samples by standard methods. The optimum peptide density was achieved with a mixture of 10% Fmoc-L-alanine/90% t-Boc-L-alanine, yielding a density of approximately 0.1 to 0.2 mmole/g resin.

Rink resin (Novobiochem) was used for syntheses when soluble, purified peptides were required as soluble binding ligands. Peptides were cleaved and deprotected, then purified by preparative reverse phase HPLC. Alternatively, some peptides required for affinity chromatography were deprotected and cleaved from Rink resin without removal of the N-terminal Fmoc group, purified by reverse phase HPLC and coupled to the appropriate affinity resin. Purity of soluble peptides was assessed by analytical reverse phase HPLC and molecular weights confirmed by FAB mass spectrometry.

Analytical Methods

Sodium dodecylsulfate polyacrylamide gel electrophoresis (SDS-PAGE) was performed in 8% or 12% polyacrylamide gels (Novex, San Diego, Calif.) according to the procedure of Laemmli (1970). Transfer of protein from gels was performed by the method of Towbin et al. (1979) using casein (Pierce Chemical Colo.) to block unused membrane binding sites. Bound antibodies were detected by using the chemiluminescent substrate CSPD (Tropix, Bedford, Mass.) and exposure to XAR film (Eastman Kodak, Rochester, N.Y.).

Immunonephelometry was performed by using a Behring Nephelometer, model BNA, with assay kits purchased from Behringwerke AG (Marburg, DEU).

Thrombin activity was measured using the synthetic substrate S-2238 (H-D-Phe-Pip-Arg-p-Nitroanaline●2HCl) (Pharmacia, Franklin, Ohio).

Discovery Of Binding Peptides To Thrombin

An assay was used to deduce peptides that bind both prothrombin and α-thrombin. Briefly, a combinatorial peptide library was synthesized directly onto a TosoHaas chromatography resin, Toyopearl AF Chelate 650 M (modified as per Buettner) at a final peptide density of approximately 0.4 mmol/g resin. The library was synthesized using F-moc chemistry with 18 of the 20 natural amino acids (cysteine and methionine were not included).

The first addition to the library (0.5 ml) was the equilibration buffer (10 mM HEPES, pH 6.8 and 0.1 M NaCl, 1.0 mM EGTA and 0.1% v/v Tween-20), and then the wash buffer (equilibration buffer containing 1 M NaCl). This was followed by sequentially contacting the resin with the individual components of the detection system. These components were, namely, anti-human thrombin antibody made in mouse, then goat anti-mouse IgG antibody conjugated with alkaline phosphatase and staining with a BCIP/NBT color system (blue). The second contacting was initiated with 1 μM α-thrombin (1 nmole total) in equilibration buffer, followed by the detection system and staining with Fast Red, as outlined above and described in more detail in Buettner, et al. (1996).

TABLE 1

Amino acid assignments from N-terminal sequencing of red beads.

| Bead Number | Sequences | | | | | | SEQ ID NO |
|---|---|---|---|---|---|---|---|
| | Q | L | W | G | S | H | 1 |
| 4-4-14 | P | F | P | Y | G | W | 2 (P/G); 3(V/G) |
| | V | | | | A | | 4 (P/A); 5(V/A) |
| | | | | | V | | 6 (P/V); 7(V/V) |
| 4-4-15 | V | T | P | F | A | V | 8 |
| | L | | | | | | 9 |
| | Y | | | | | | 10 |
| 4-3-21 | L | F | A | P | T | L | 11 |
| | P | | | | | | 12 |
| 4-4-27 | S | V | R | P | F | L | 13 |
| 9-3 | F | E | P | A | N | P | 14 |
| 8-8 | G | F | R | K | G | P | 15 |
| | | | | N | | | 16 |
| 10-3 | E | R | P | Y | H | G | 17 |
| | | | | | K | | 18 |
| T16 | Y | F | P | G | P | Y | L 19 |

Blue beads, which indicated non-specific interactions with the detection system, were uniformly found throughout the column at <0.1%; ten beads stained red. Individual red beads were isolated manually and sonicated for 20 minutes in methanol to remove the insoluble red dye. The immobilized peptides were sequenced by Edman degradation and are given in Table 1. For cycles where there were ambiguous calls, the amino acids with the highest responses are listed on the first line, and those with lower yields on subsequent lines.

Confirmatory binding assays were performed in a column chromatographic format on a microbore HPLC using individual peptide sequences synthesized directly onto the Toyopearl 650 M Chelate resin which had been modified with Totda followed by an alanine residue (A-Totda-Toyopearl), at a final substitution density of 0.2 mmol/g resin. Contactings to these resins included A) equilibration buffer (as above), wash buffer (as above), high salt buffer (equilibration buffer containing 3 M NaCl), and elution buffer (2.5 % acetic acid) only; B) human serum albumin in equilibration buffer (hSA; 0.5 mg), followed by wash, high salt, and elution buffers, C–E) graded doseages (50, 100, and 200 μg) of purified α-thrombin in equilibration buffer, followed by wash, high salt, and elution buffers. The endpoint was a dose-dependent increase in the acid eluate in the thrombin contactings, and quantification was by integration of the absorbance at 280 nm. Integration of eluates from all peptide resins are presented in Table 2.

Several sequences derived from positive red beads from the PELICAN screening bound thrombin in a dose dependent manner (Table 2). Elution was effected by using low pH treatment, not by NaCl to any great extent, suggesting that the binding interactions were apparently stronger than the hirudin-derived peptide. Those peptides which bound thrombin were QLWGSH (as well as variants having an additional R or H inserted before the Q), PFPYGW (and all variants, VFPYGW, PFPYAW, VFPYAW, PFPYVW, and VFPYVW), YTPFAV (but not the variants substituting V or L for Y at the first position), LFAPTL (but not PFAPTL), SVRPFL, FEPANP, GFRKGP (and GFRNGP), ERPYKG (but not ERPYHG), and YFPGPYL. Peptide resin containing PFPYVW bound thrombin but not in a dose dependent manner. (See Table 2 for SEQ ID NOs)

TABLE 2

Binding analysis of peptides synthesized on A-Totda-Toyopearl.

Figure 1:
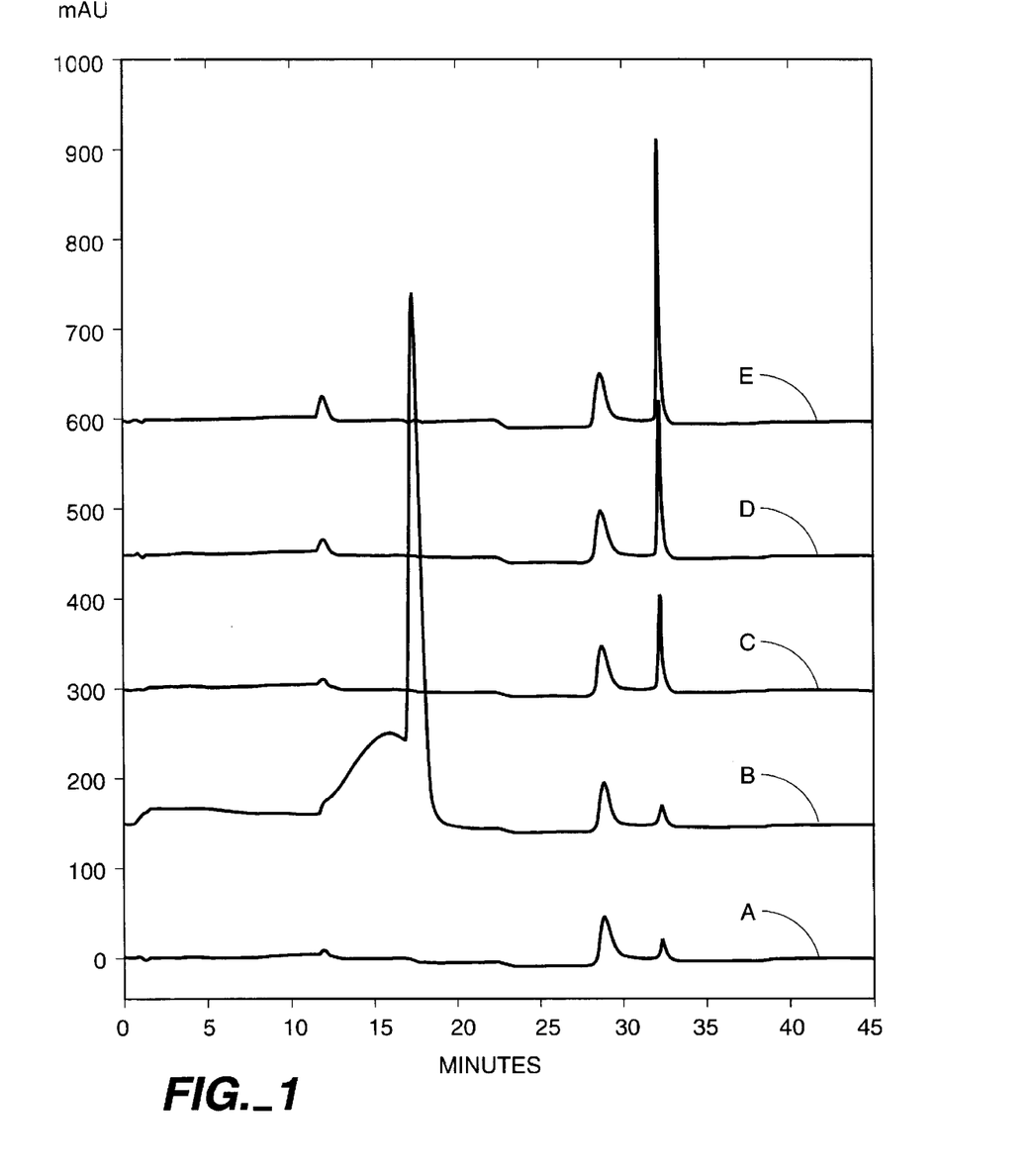
FIG. 1 shows elution profiles (absorbance at 280 nm) of chromatographic separations on peptide QLWGSH-A-Totda-Toyopearl. (SEQ ID NO 1) A) buffers, no protein; B) 0.5 mg hSA; C) 50 µg thrombin; D) 100 µg thrombin; E) 200 µg thrombin. Protein was applied at approximately 17 µl/min for 10 minutes, and then the column was washed with equilibration buffer for 4 minutes at 865 µl/min. This was followed by equilibration buffer containing 1.0 M NaCl for 5 minutes, 3.0 M NaCl for a further 5 minutes, and 0.1 M for another 5 minutes. Protein was eluted between 30 and 35 minutes using 2% acetic acid.

| | | Absorbance, 280 nm | | | | | |
|---|---|---|---|---|---|---|---|
| | | 1M NaCl Eluate | | | | | |
| | PEPTIDE | μg α-Thrombin Applied | | | 2% Acetic Acid μg α-Thrombin Applied | | |
| SEQ ID NO | SEQUENCES | 50 | 100 | 200 | 50 | 100 | 200 |
| 1 | QLWGSH | np | np | np | 1.54 | 3.23 | 6.92 |
| 1 | QLWGSH | 0.06 | 0.05 | 0.08 | 1.39 | 2.09 | 3.71 |
| 2 | PFPYGW | np | np | np | 0.47 | 0.79 | 1.37 |
| 3 | VFPYGW | np | np | np | 0.88 | 1.46 | 2.01 |
| 4 | PFPYAW | np | np | np | 0.50 | 1.05 | 1.10 |
| 5 | VFPYAW | 0.16 | 0.18 | np | 1.48 | 1.57 | 3.59 |
| 6 | PFPYVW | np | np | np | 2.82 | 2.14 | 3.32 |
| 7 | VFPYVW | np | np | np | 0.81 | 1.21 | 1.81 |
| 8 | VTPFAV | np | np | np | 0.00 | 0.00 | 0.00 |
| 9 | LTPFAV | np | np | np | 0.00 | 0.00 | 0.00 |
| 10 | YTPFAV | np | np | np | 0.16 | 0.28 | 0.34 |
| 11 | LFAPTL | np | np | np | 0.18 | 0.44 | 1.25 |
| 12 | PFAPTL | np | np | np | np | np | np |
| 13 | SVRPFL | np | np | np | 0.57 | 0.71 | 2.06 |
| 14 | FEPANP | 0.00 | 0.00 | 0.10 | 0.15 | 0.29 | 0.45 |
| 15 | GFRKGP | 0.12 | 0.15 | 0.25 | 0.41 | 0.77 | 1.71 |
| 16 | GERNGP | 0.00 | 0.00 | 0.13 | 0.71 | 1.42 | 2.73 |
| 17 | ERPYHG | 0.00 | 0.18 | 0.69 | 0.00 | 0.00 | 0.00 |
| 18 | ERPYKG | 0.23 | 0.23 | 0.26 | 0.41 | 0.99 | 2.38 |
| 19 | YFPGPYL | * | * | * | 2.10 | 2.93 | 4.72 |
| 20 | RQLWQSH | np | np | np | 0.75 | 1.49 | 2.83 |
| 21 | HQLWGSH | np | np | np | 0.58 | 0.95 | 1.76 | np = no peak, i.e., no visible A280 signal and no subsequent integration.
*α-thrombin applied in a solution containing 5 mg/ml hSA, therefore 1M NaCl peak integration cannot be attributed to α-thrombin Peptide resin QLWGSH was chosen for further study (SEQ ID NO 1). The binding and elution profile of purified α-thrombin (50, 100 and 200 μg) is shown in FIG. 1. There was a dose dependent increase in the acid eluant (FIG. 1 C, D and E). Fractions were collected for assay of thrombin activity by using the chromogenic substrate S2238. Approximately 64 to 79% of the applied α-thrombin esterase activity was recovered in the acid eluant following adjustment of the pH to neutrality (Table 3). Much smaller amounts of activity eluant in the unbound fraction (not shown) and in the 3 M NaCl eluant. Point additions of arginine and histidine onto the amino terminus allowed for enhanced binding (SEQ ID NOs:20 and 21).

Figure 5:
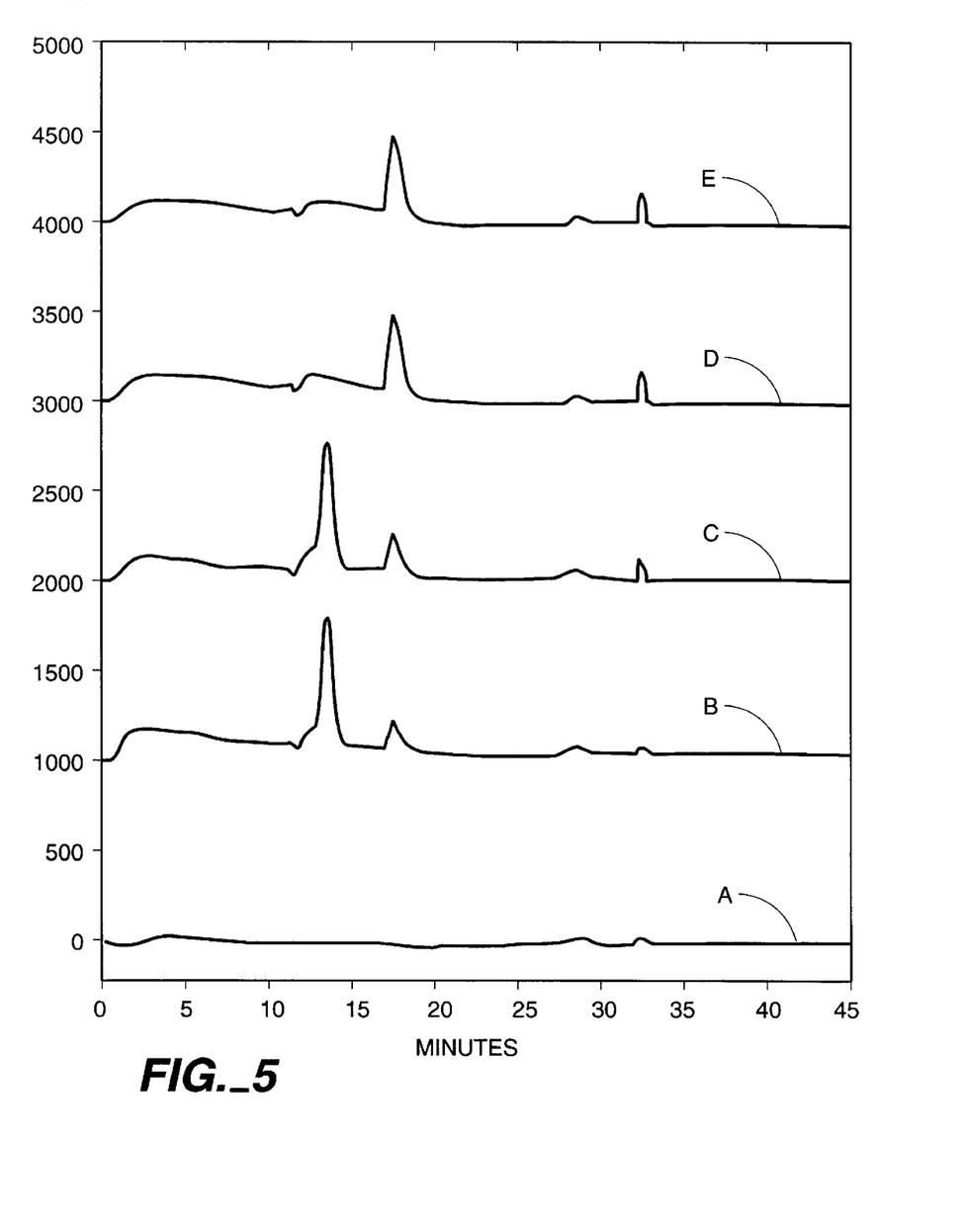
FIG. 5 shows elution profiles (absorbance at 280 nm) of chromatographic separations on peptide YFPGPYL-Totda-Toyopearl (SEQ ID NO:19). A) buffers, no protein; B) 0.5 mg hSA; C) 0.5 mg hSA+50 µg thrombin; D) 0.5 mg hSA+100 µg thrombin; E) 0.5 mg hSA+200 µg thrombin. Running conditions were as described for FIG. 1.

Peptide resin YFPGPYL (SEQ ID NO:19) was chosen for further study based on the binding and elution profiles for a mixture of purified α-thrombin and hSA (0.5% v/v) shown in FIG. 5. There was a dose dependent increase in acid eluant (FIG. 5C, D, and E).

TABLE 3

Recovery of α-thrombin activity.

| α-Thrombin Input, μg | α-Thrombin Activity, μg (%) | |
|---|---|---|
| | 3M NaCl Wash | 2% HAc Eluate |
| 50 | 4.1 (8.2) | 34.7 (69.3) |
| 100 | 6.5 (6.5) | 78.7 (78.7) |
| 200 | 10.7 (5.3) | 128 (63.9) |

EXAMPLE 1

Purification Of α-Thrombin From Activated Prothrombin Complex (PTC) Eluate By Using QLWGSH Resin (SEQ ID NO:1)

Figure 2:
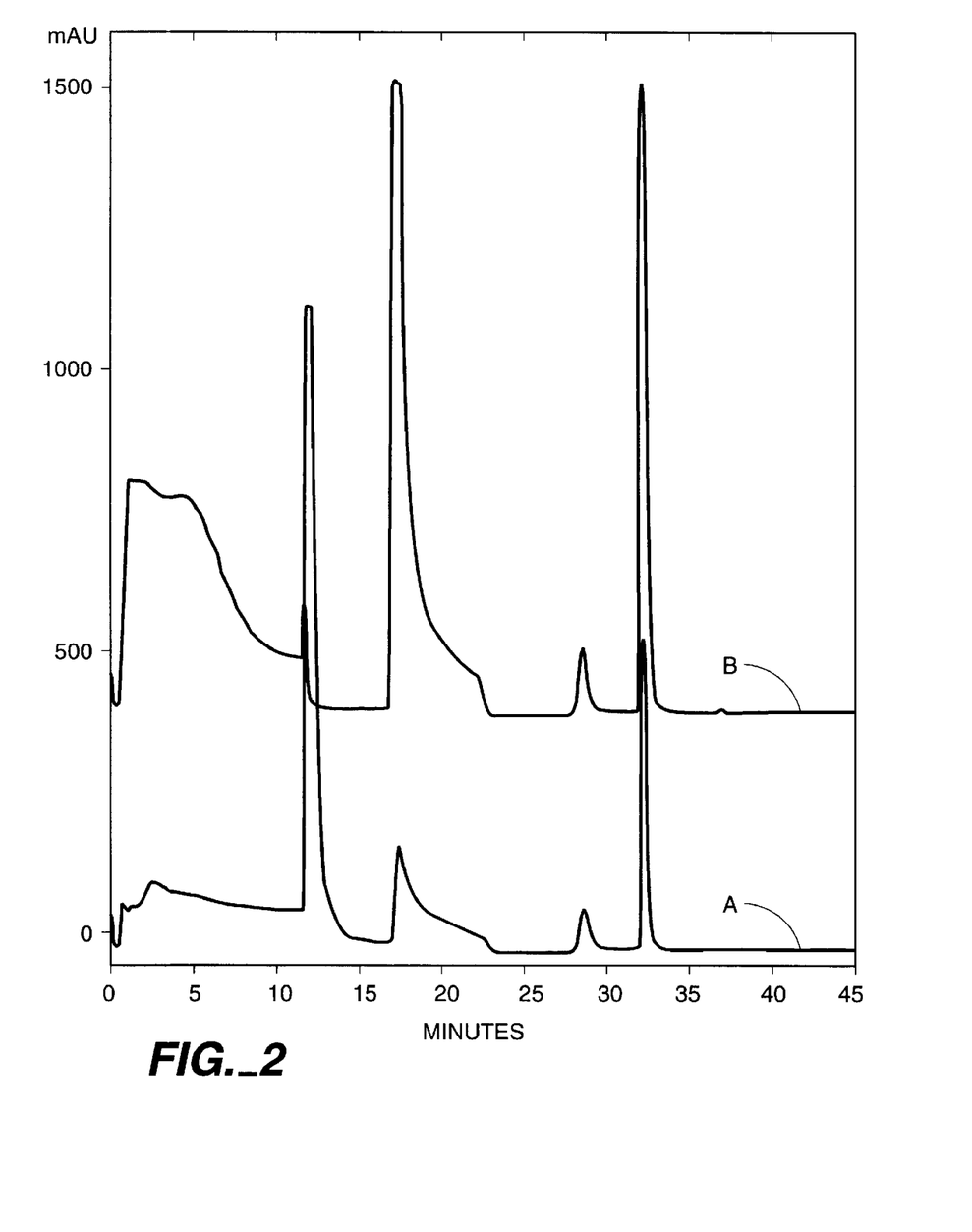
FIG. 2 shows elution profiles (absorbance at 280 nm) of chromatographic separations of activated and unactivated PTC eluate on peptide QLWGSH-A-Totda-Toyopearl. A) activated PTC eluate; B) unactivated PTC eluate. Running conditions were as described for FIG. 1.

Human pooled plasma was processed to PTC eluate by standard manufacturing techniques. In brief, DEAE-Sephadex resin was added to post cryoprecipitate eluant and loosely bound protein was washed away with a low salt buffer. Higher concentrations of NaCl eluted the fraction called PTC eluate which contains prothrombin and the vitamin K-dependent coagulation protease zymogens (factors VII, IX, X, protein C and protein S). A sample of PTC eluate was activated in the presence of 25% (w/w) sodium citrate for 4 days at room temperature. Approximately 1.0 ml of activated PTC eluate was injected onto the peptide resin QLWGSH-A-Totda-Toyopearl (FIG. 2 A). The column was washed with equilibration buffer (10 mM HEPES, pH 6.8, 1.0 mM EGTA and 0.1% v/v Tween-20) containing 1.0 M NaCl and then washed further with equilibration buffer containing 3.0 M NaCl. Acid treatment (2.5% acetic acid) was used to release protein from the peptide resin.

Figure 3A:
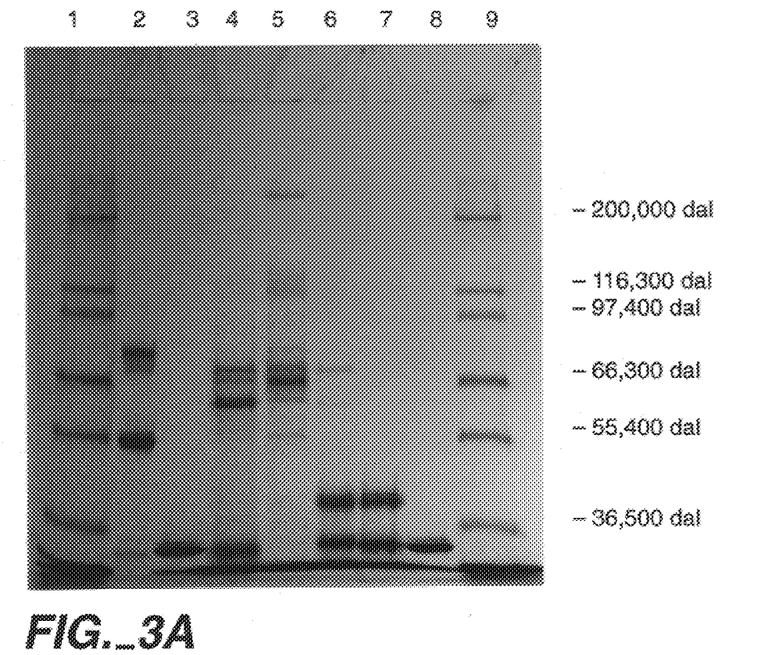
FIG. 3A and 3B show the SDS-PAGE (8 % polyacrylamide gel) and western blot analyses of fractions from the chromatographic separation of activated PTC eluate on QLWGSH-A-Totda-Toyopearl. Panel A: Coomassie-stained gel, Panel B: Western blot using antibody to α-thrombin.
Figure 3B:
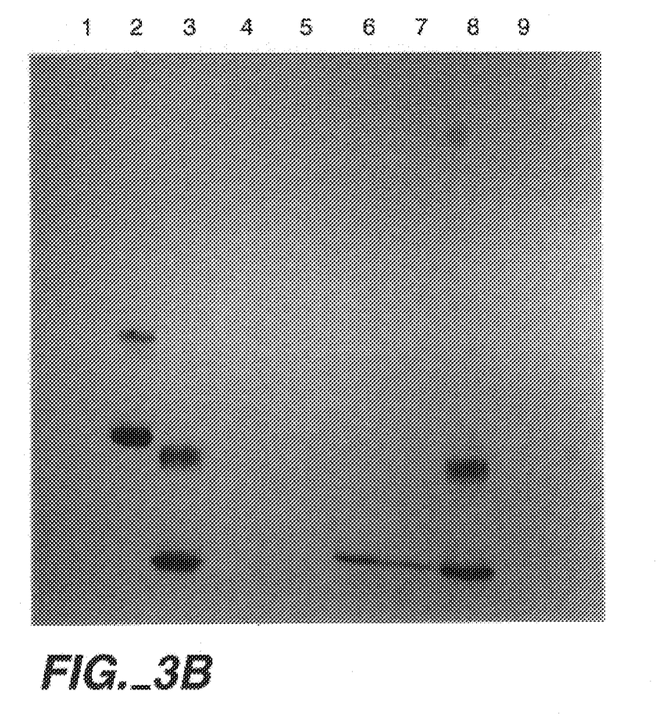

QLWGSH-A-Totda-Toyopearl bound protein from activated PTC eluate (FIG. 2A). A lesser amount of protein bound to the resin which was released by either NaCl or acid treatment. By SDS-PAGE and western blotting (FIG. 3 A and B), the activated PTC eluate was depleted of thrombin by passage through the column (see lane 5, unbound fraction). Both 1 M NaCl and 2.5% acetic acid contained highly enriched thrombin (FIG. 3 A and B, lanes 6 and 7). A similar amount of thrombin was eluted with 3 M NaCl (not shown). A second polypeptide with an apparent molecular weight of approximately 42,000(as determined by migration in SDS-PAGE) co-eluted with thrombin but did not react with antibody to thrombin. N-terminal sequence analysis of this polypeptide did not result in a discernable sequence. This suggests that QLWGSH bound and enriched thrombin.

EXAMPLE 2

Purification Of Prothrombin From Prothrombin Complex (PTC) Eluate By Using QLWGSH Resin (SEQ ID NO 1)

Human pooled plasma was processed to PTC eluate by standard manufacturing procedures as indicated in Example 1. Approximately 1.0 ml of PTC eluate was injected onto the peptide resin QLWGSH-A-Totda-Toyopearl (FIG. 2 B). The column was washed with equilibration buffer containing 1.0 M NaCl and then containing 3.0 M NaCl. Acid treatment (2.5% acetic acid) was used to release protein from peptide resin.

Figure 4A:
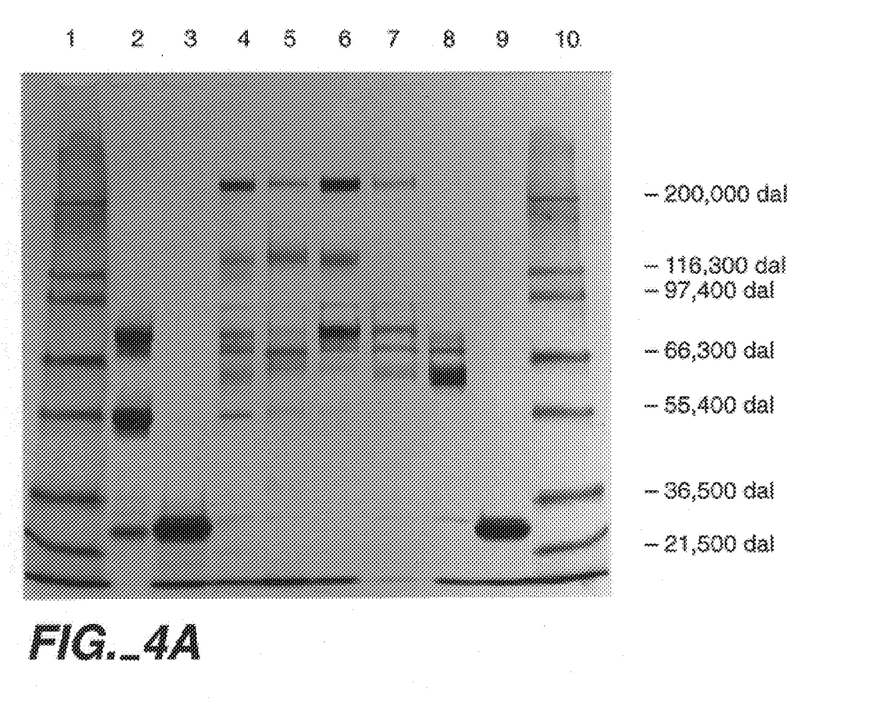
FIG. 4A and 4B shows the SDS-PAGE (8% polyacrylamide gel) and western blot analyses from the chromatographic separation of PTC eluate on QLWGSH-A-Totda-Toyopearl. Panel A: Coomassie-stained gel, Panel B: Western blot using antibody to α-thrombin. Lanes 1 and 10, molecular weight standards; lane 2, prothrombin standard; lanes 3 and 9, α-thrombin standards; lane 4, PTC eluate; lane 5, unbound fraction; lane 6, 1 M NaCl wash fraction; lane 7, 3 M NaCl wash fraction; lane 8, 2% acetic acid eluate.
Figure 4B:
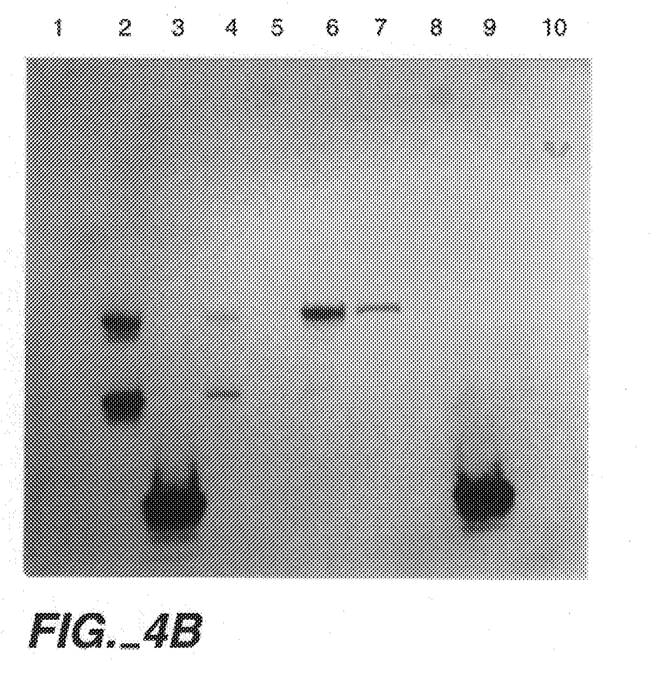

QLWGSH-A-Totda-Toyopearl bound protein from unactivated PTC eluate. A large portion of the total protein (by $A_{280}$) was released by 1 M NaCl (FIG. 2B) which was enriched in prothrombin (FIG. 4 A and B) by SDS-PAGE and western blot analysis. A smaller amount of prothrombin was released by 3 M NaCl (FIG. 2 B and FIG. 4 A and B). Acid elution released at least three polypeptides, none of which reacted with antibody to thrombin. These results demonstrated that prothrombin bound the peptide QLWGSH and could be released from the peptide with an enriched purity by elution with buffer containing 1 M NaCl.

EXAMPLE 3

Purification Of α-Thrombin From Activated Prothrombin Complex (PTC) Eluate By Using YFPGPYL Resin (SEQ ID NO:19)

Figure 6:
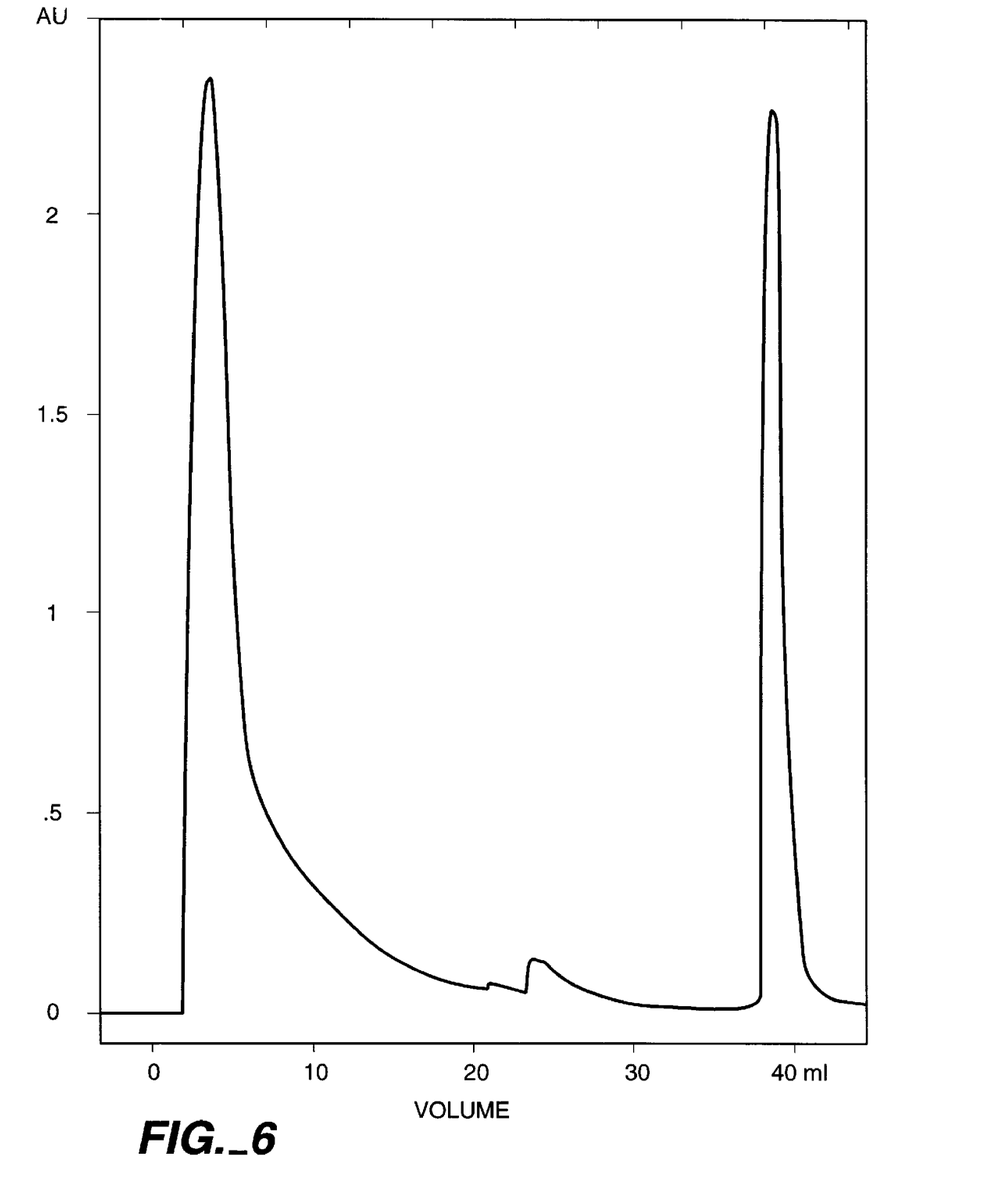
FIG. 6 shows an elution profile (absorbance at 280 nm) of a chromatographic separation of activated PTC eluate on peptide YFPGPYL-Totda-Toyopearl. Equilibration (10 mM HEPES pH 6.5, 10 mM $CaCl_2$, 0.1% (v/v) PEG-400, 500 mM NaCl) is from 0.0 ml to 18.6 ml; 1 mM sodium citrate pH 7.0 is from 18.6 ml to 34.1 ml; 2% acetic acid is from 34.1 ml to 43.4 ml.

Human pooled plasma was processed to PTC eluate by standard manufacturing procedures as indicated in Example 1. A sample of the PTC eluate was activated in the presence of 50 mM $CaCl_2$ for 6 days at 4° C. Approximately 1 ml of the activated PTC eluate, spiked with 300 μg α-thrombin, was injected onto the peptide resin YFPGPYL-Totda-Toyopearl (FIG. 6). The column was washed with equilibration buffer (10 mM HEPES, pH 6.5, 10 mM $CaCl_2$, 500 mM NaCl, 0.1% (v/v) PEG-400) until the $A_{280}$ returned to base-line. The peptide column was then washed with 1 mM sodium citrate pH 7.0 to release the a-thrombin bound to the peptide. Acid treatment (2% acetic acid) was used as a cleaning step to remove protein still bound to the column.

Figure 7:
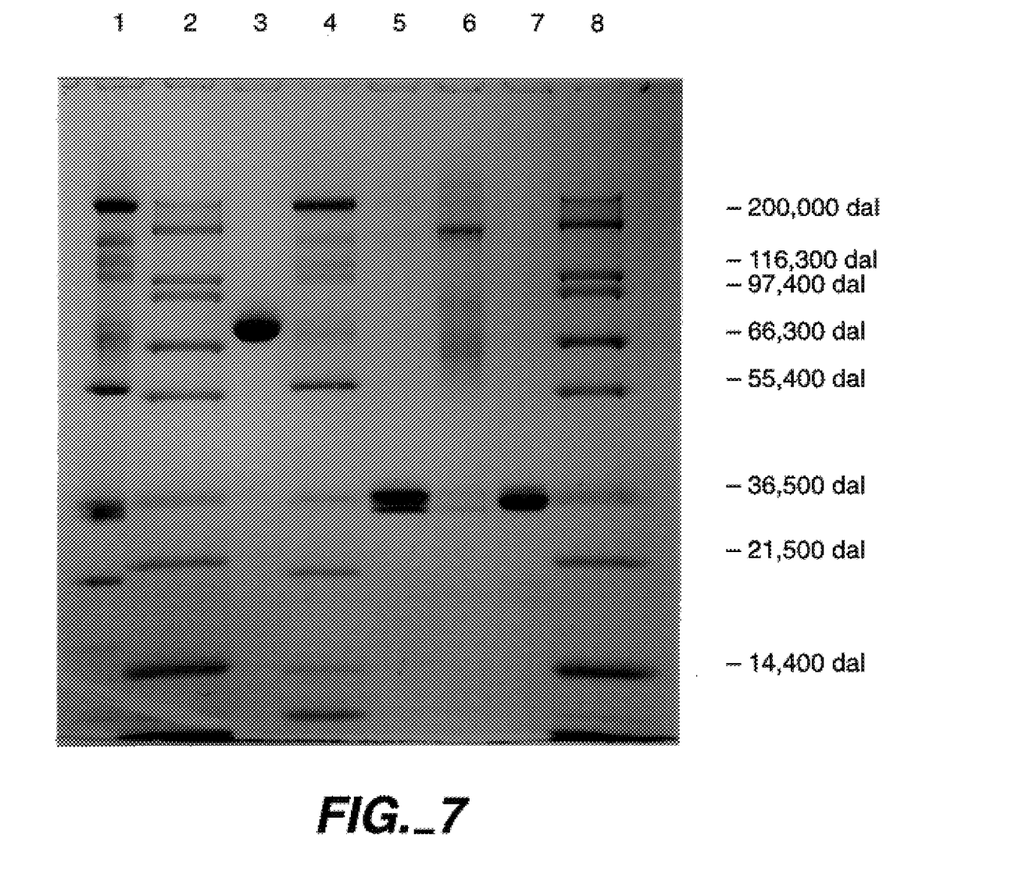
FIG. 7 shows the Coomassie-stained SDS-PAGE (12% polyacrylamide gel) from the chromatographic separation of activated PTC eluate on YFPGPYL-Totda-Toyopearl. Lane 1, 6 day $CaCl_2$-activated PTC eluate spiked with 300 µg α-thrombin; lanes 2 and 8, molecular weight standards; lane 3, prothrombin standard (MW ~71,600); lane 4, unbound fraction; lane 5, 1 mM sodium citrate pH 7.0 fraction; lane 6, 2% acetic acid fraction; lane 7, α-thrombin standard (MW ~37,000).

The peptide column YFPGPYL-Totda-Toyopearl bound protein from the α-thrombin-spiked PTC eluate. The majority of the total protein (by $A_{280}$) flowed through the column and a lesser amount was released by 1 mM sodium citrate pH 7.0 (FIG. 6). The protein released by 1 mM sodium citrate pH 7.0 was at least 72% thrombin, as indicated by quantitative scanning analyses of SDS-PAGE (FIG. 7). Other minor contaminants were higher in molecular weight and do not appear to be degradation products of thrombin. Acid treatment removed a smaller amount of thrombin and larger amounts of higher molecular weight protein species. These results demonstrated that the activated serine protease thrombin bound YFPGPYL and could be released from the peptide in a specific manner resulting in enrichment.

CONCLUSION

Screening a combinatorial library with α-thrombin using PELICAN technology resulted in the discovery of binding peptides useful for affinity chromatography. Affinity resin containing peptide ligand QLWGSH (SEQ ID NO:1) bound and purified either prothrombin or thrombin, depending on the source of protein. Affinity resin containing the peptide ligand YFPGPYL (SEQ ID NO:19) bound and purified thrombin from activated PTC eluate.

Additionally, binding and retention of these proteins to QLWGSH resin ocurred in the presence of Tween-20, a non-ionic detergent useful for inactivating enveloped viruses that could potentially contaminate human plasma fractions. Thus, this resin would be useful for removal of viral inactivating detergents from (pro)thrombin during processing, or even useful for treatment of (pro)thrombin with detergent to inactivate viruses while bound to the affinity resin.

The above examples are intended to illustrate the invention and it is thought variations will occur to those skilled in the art. Accordingly, it is intended that the scope of the invention be limited only by the claims below.

REFERENCES

Buettner, J. A. et. al., Int. J. Protein Pept. Res. 47: 70–83 (1996).

Coan, M. H., et al., Ann. NY Acad. Sci. 370: 731–746 (1981).
De Marco, L. et al., J. Biol. Chem. 269: 6478–6484 (1994).
Downing, M. R., et al., J. Biol. Chem. 250: 8897–8906 (1975).
Fenton, J. W., II, et al., Biochim. Biophys. Acta 229: 26–32 (1971).
Fenton, J. W., II, et al., J. Biol. Chem. 252: 3587–3598 (1977).
Khamlichi, S., D. et al., J. Chromatogr. 510: 123–1312 (1990).
Krstenansky, J. L., et al., J. Med. Chem. 30: 1688-(1987)
Lorne, J. L, et al., Rev. Fr. Transfus. Hemobiol. 32: 391–402 (1989).
Miller, K. D., and W. H. Copeland, Exp. Mol. Pathol. 4: 431–437 (1965).
Miller-Anderson, M., et al., Thromb. Res. 20: 109–122 (1980).
Ngai, P. K, and J.-Y. Chang, Biochem. J. 280: 805–808 (1990).
Peters, K., et al., J. Chromatog. 648: 91–99 (1993).
Thompson, A. R., Biochim. Biophys Acta 422: 200–209 (1976).
Thompson, A. R., and E. W. Davie, Biochim. Biophys. Acta 250: 210–215 (1971).
Walz, D. A., and W. H. Seegers, Biochem, Biophys. Res. Commun. 60: 717–722 (1974).
Yu, X. J., et al., J. Chromatog. 376: 429–435 (1986).

What is claimed is:

1. A composition comprising a peptide, wherein the peptide has a defined sequence selected from the group consisting of Gln-Leu-Trp-Gly-Ser-His, Arg-Gln-Leu-Trp-Gly-SerHis, His-Gln-Leu-Trp-Gly-Ser-His, and Tyr-Phe-Pro-Gly-Pro-Tyr-Leu.

2. A method of purifying a protein selected from the group consisting of prothrombin and thrombin, wherein the method comprises contacting an aqueous solution containing the protein with a substrate under conditions sufficient to bind the protein to the substrate, wherein the substrate comprises peptides of a defined sequence bound to a support material, wherein the defined sequence is selected from the group consisting of Gln-Leu-Trp-Gly-SerHis, Arg-Gln-Leu-Trp-Gly-Ser-His, His-Gln-Leu-Trp-Gly-Ser-His, and Tyr-Phe-Pro-GlyPro-Tyr-Leu.

* * * * *